(12) United States Patent  
Harjes et al.

(10) Patent No.: US 11,590,336 B2  
(45) Date of Patent: Feb. 28, 2023

(54) SYSTEMS AND METHODS FOR EVALUATING BLOOD BEHAVIOR WHEN FLOWING THROUGH IMPLANTABLE MEDICAL DEVICES

(71) Applicant: TC1 LLC, St. Paul, MN (US)

(72) Inventors: Dan Harjes, Carlisle, MA (US); Balakrishnan Sivaraman, Nashua, NH (US)

(73) Assignee: TC1 LLC, St. Paul, MN (US)

( * ) Notice: Subject to any disclaimer, the term of this patent is extended or adjusted under 35 U.S.C. 154(b) by 457 days.

(21) Appl. No.: 16/809,172

(22) Filed: Mar. 4, 2020

(65) Prior Publication Data

US 2020/0282122 A1  Sep. 10, 2020

Related U.S. Application Data

(60) Provisional application No. 62/813,992, filed on Mar. 5, 2019.

(51) Int. Cl.
| | |
|---|---|
| *A61M 60/113* | (2021.01) |
| *A61M 60/178* | (2021.01) |
| *A61M 60/859* | (2021.01) |
| *A61M 60/88* | (2021.01) |
| *A61M 60/585* | (2021.01) |

(52) U.S. Cl.
CPC ........ *A61M 60/113* (2021.01); *A61M 60/178* (2021.01); *A61M 60/585* (2021.01); *A61M 60/859* (2021.01); *A61M 60/88* (2021.01); *A61M 2202/0413* (2013.01); *A61M 2205/3368* (2013.01); *A61M 2205/366* (2013.01)

(58) Field of Classification Search
CPC .............. A61M 60/585; A61M 60/859; A61M 60/178; A61M 60/113; A61M 60/88; A61M 2202/0413; A61M 2250/3334; A61M 2250/3368; A61M 2250/3379; A61M 2250/366; A61M 1/36; A61M 1/3632

See application file for complete search history.

(56) References Cited

U.S. PATENT DOCUMENTS 4,240,294 A * 12/1980 Grande ..................... G01F 1/38  
73/861.47  
4,643,713 A * 2/1987 Viitala ................ A61M 1/3627  
96/155

(Continued)

*Primary Examiner* — Philip R Wiest  
(74) *Attorney, Agent, or Firm* — Armstrong Teasdale LLP

(57) ABSTRACT

Systems and methods for evaluating blood behavior when flowing through an implantable medical device are provided. A flow loop includes the implantable medical device, and a blood reservoir configured to contain a volume of blood and to supply blood from the volume of blood to the implantable medical device. The flow loop further includes a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter, and a flow diverter coupled in flow communication between the plurality of tubing sections and the blood reservoir, the flow diverter comprising an outlet that is configured to be positioned below a surface of the volume of blood.

20 Claims, 2 Drawing Sheets

(56) References Cited

U.S. PATENT DOCUMENTS

| | | | |
|---|---|---|---|
| 2002/0085952 A1* | 7/2002 | Ellingboe | A61M 1/3621 |
| | | | 604/4.01 |
| 2007/0213690 A1* | 9/2007 | Phillips | A61M 1/3653 |
| | | | 604/533 |
| 2017/0049945 A1* | 2/2017 | Halvorsen | A61M 60/178 |
| 2017/0224894 A1* | 8/2017 | Najar | A61M 60/38 |
| 2020/0246526 A1* | 8/2020 | Menon | A61M 60/859 |

* cited by examiner

SYSTEMS AND METHODS FOR EVALUATING BLOOD BEHAVIOR WHEN FLOWING THROUGH IMPLANTABLE MEDICAL DEVICES

CROSS REFERENCE TO RELATED APPLICATIONS

This application claims priority to provisional application Ser. No. 62/813,992, filed Mar. 5, 2019, which is incorporated by reference herein in its entirety.

FIELD OF THE DISCLOSURE

This disclosure relates to evaluating blood behavior when flowing through implantable medical devices, and more particularly, this disclosure relates to flow loops that use low volumes of blood to evaluate blood behavior.

BACKGROUND

Ventricular assist systems (VASs) may include ventricular assist devices (VADs), such as implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAS while awaiting a heart transplant or as a long-term destination therapy. In another example, a patient may use a VAS while recovering from heart surgery. Thus, a VAS can supplement a weak heart (i.e., partial support) or can effectively replace the natural heart's function. VASs can be implanted in the patient's body and powered by an electrical power source inside or outside the patient's body.

To evaluate the performance of VASs and other implantable medical devices, a testing apparatus may be used to simulate the operation of a device in a patient. Specifically, at least some known testing apparatus use flow loops to repeatedly circulate fluids through an implantable medical device. The fluid may be, for example, animal blood or fresh human blood.

Fresh human blood is generally more desirable, as it more accurately simulates the conditions in an actual patient. However, fresh human blood has limited availability relative to animal blood. Further, platelets in fresh human blood disintegrate over time, limiting the amount of time that fresh human blood can be used with a testing apparatus.

Accordingly, a testing apparatus that uses less human blood and requires less time to evaluate an implantable medical device would be advantageous.

BRIEF SUMMARY OF THE DISCLOSURE

In one embodiment, the present disclosure is directed to a flow loop for evaluating blood behavior when flowing through an implantable medical device. The flow loop includes the implantable medical device, a blood reservoir configured to contain a volume of blood and to supply blood from the volume of blood to the implantable medical device, a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter, and a flow diverter coupled in flow communication between the plurality of tubing sections and the blood reservoir, the flow diverter comprising an outlet that is configured to be positioned below a surface of the volume of blood.

In another embodiment, the present disclosure is directed to a blood behavior evaluation system. The blood behavior evaluation system includes a plurality of heat exchangers, and a plurality of flow loops, wherein each flow loop of the plurality of flow loops comprises an implantable medical device, a blood reservoir configured to contain a volume of blood and to supply blood from the volume of blood to the implantable medical device, a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter, and a flow diverter coupled in flow communication between the plurality of tubing sections and the blood reservoir, the flow diverter comprising an outlet that is configured to be positioned below a surface of the volume of blood.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for evaluating blood behavior when flowing through an implantable medical device. A flow loop includes the implantable medical device, and a blood reservoir configured to contain a volume of blood and to supply blood from the volume of blood to the implantable medical device. The flow loop further includes a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter, and a flow diverter coupled in flow communication between the plurality of tubing sections and the blood reservoir, the flow diverter comprising an outlet that is configured to be positioned below a surface of the volume of blood.

Figure 1:
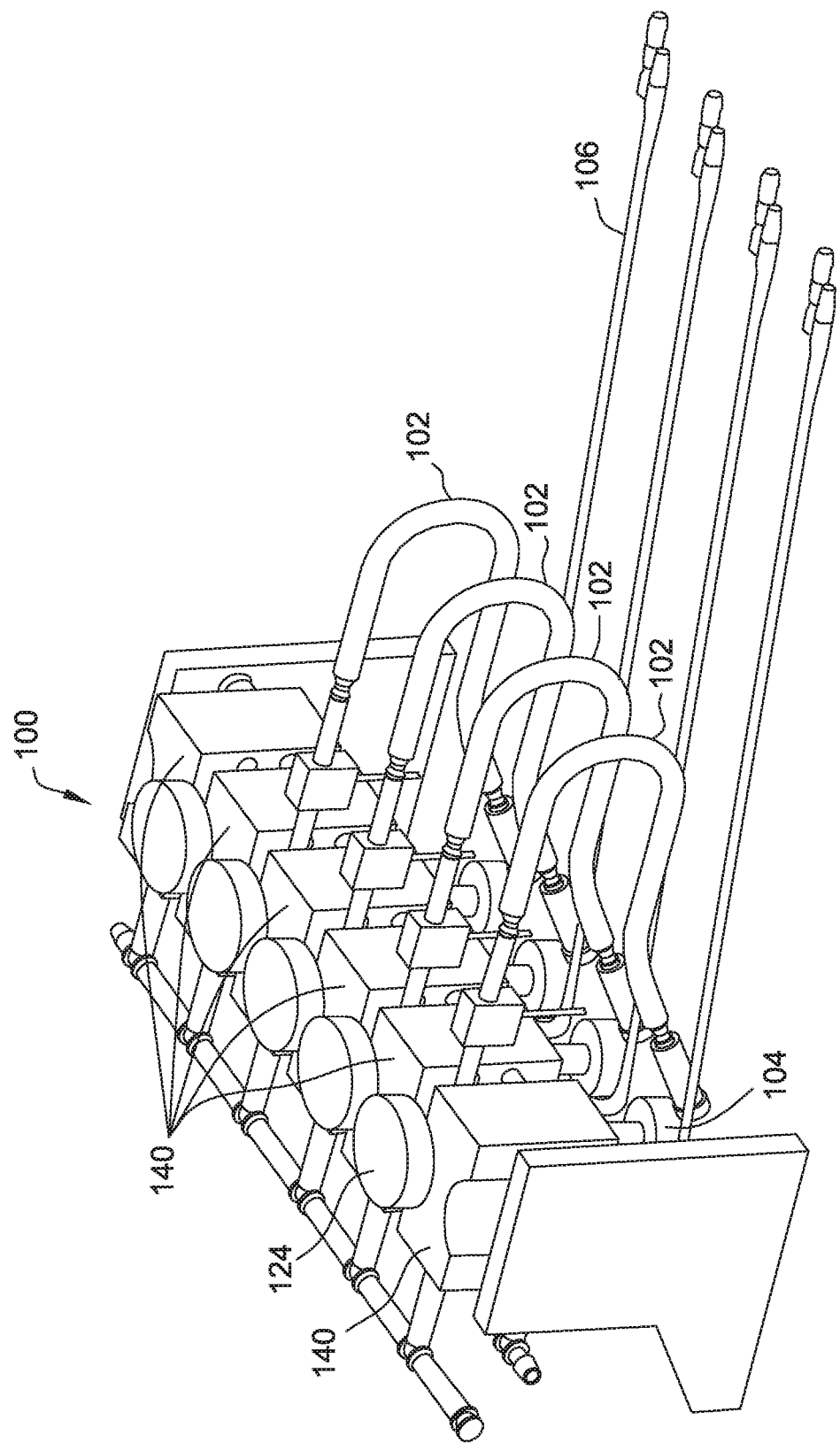
FIG. 1 is a perspective view of one embodiment of a blood behavior evaluation system including a plurality of flow loops.

Referring now to the drawings wherein like reference numerals are used to identify identical components in the various views, FIG. 1 illustrates one exemplary embodiment of blood behavior evaluation system 100 including a plurality of flow loops 102. Each flow loop 102 may be used to evaluate blood behavior when flowing through a respective implantable medical device. Accordingly, blood behavior evaluation system 100 facilitates evaluating blood behavior when flowing through a plurality of implantable medical devices simultaneously. In the embodiment shown in FIG. 1, blood behavior evaluation system 100 includes four flow loops 102. Alternatively, blood behavior evaluation system 100 may include any suitable number of flow loops 102.

Figure 2:
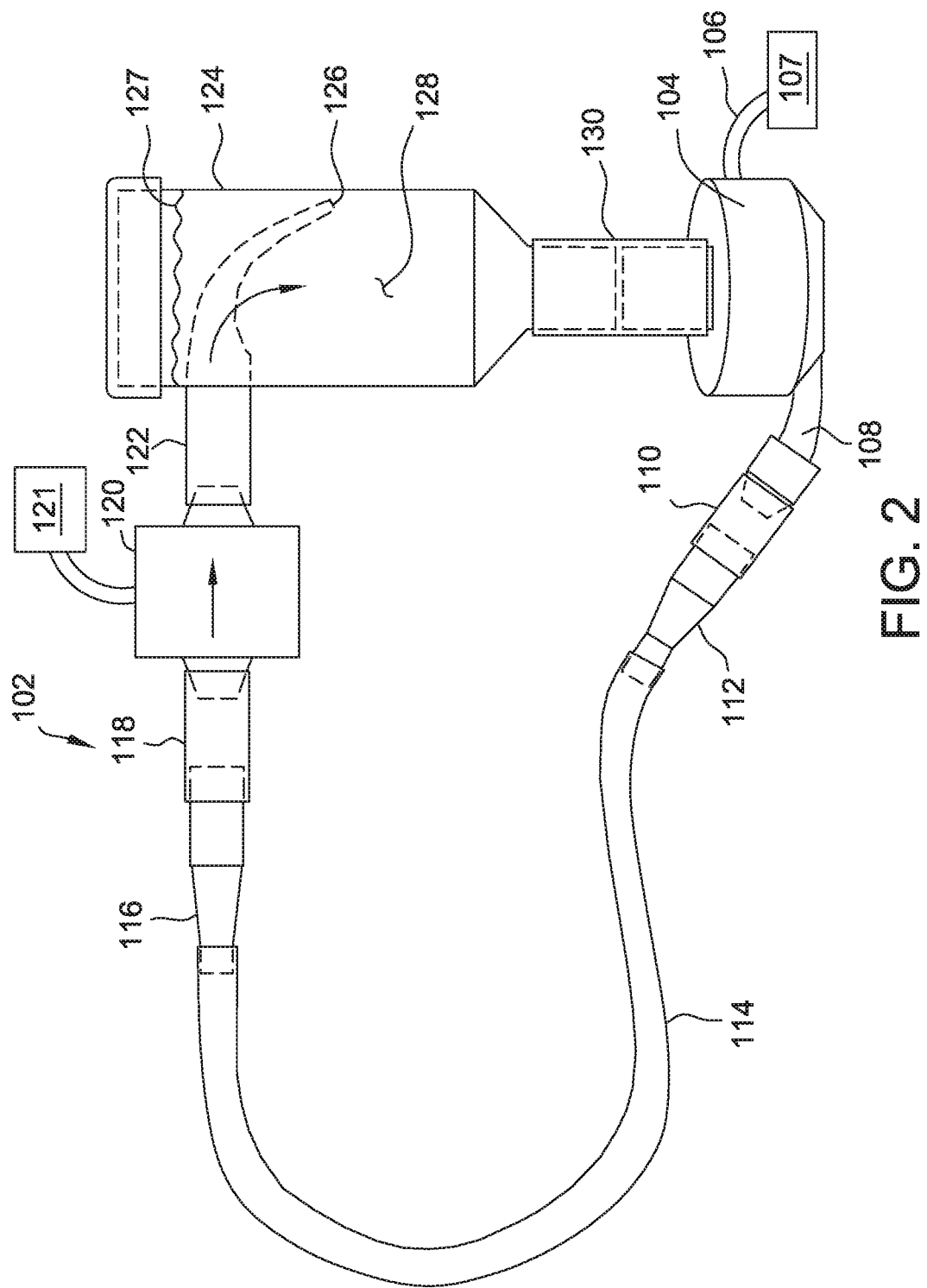
FIG. 2 is a schematic diagram of one embodiment of a flow loop that may be used with the blood behavior evaluation system shown in FIG. 1.

FIG. 2 is a schematic diagram of one flow loop 102 that may be used with blood behavior evaluation system 100. As shown in FIG. 2, flow loop 102 is a closed-loop including a plurality of different components. Blood is circulated through components of flow loop 102 as described herein. With respect to FIG. 2, the blood circulates through flow loop in a generally clockwise direction.

Flow loop 102 is used to evaluate blood behavior when flowing through an implantable medical device. More specifically, in this embodiment, flow loop 102 is used to evaluate blood behavior when flowing through a left ventricular assist device (LVAD) 104. LVAD 104 is implantable in a patient to assist the patient's left ventricle in pumping blood to the rest of the patient's body. LVAD 104 may be, for example, a HEARTMATE II® or HEARTMATE LVAD. HEARTMATE II® and HEARTMATE 3® are registered trademarks of Thoratec Corporation, of Pleasanton, Calif. Alternatively, LVAD 104 may be any LVAD or other implantable medical device suitable for use with flow loop 102 (e.g., medical devices included in other ventricular assist systems). As shown in FIGS. 1 and 2, each LVAD 104 includes a driveline cable 106 that delivers signals to LVAD 104 (e.g., from an external controller 107) to control operation of LVAD 104 (e.g., by controlling a pump speed of LVAD 104).

Referring back to FIG. 2, LVAD 104 includes a barbed outflow conduit 108. Barbed outflow conduit 108 is coupled in flow communication with a first tubing section 110, such that LVAD 104 pumps blood through barbed outflow conduit 108 into first tubing section 110. In this embodiment, first tubing section 110 is a section of flexible polymer tubing, such as TYGON® tubing. TYGON® is a registered trademark of Saint-Gobain Performance Plastics Corporation, of Solon, Ohio. Further, in this embodiment, first tubing section 110 has a diameter of approximately 0.375 inches (9.525 millimeters (mm)) and a length in a range from approximately 1.0 inches (25.4 mm) to 4.0 inches (101.6 mm) (e.g., a length of 2.0 inches (50.8 mm)). Alternatively, first tubing section 110 may have any composition and dimensions that enable flow loop 102 to function as described herein.

First tubing section 110 is coupled in flow communication with a first tubing adaptor 112. In this embodiment, first tubing adaptor 112 transitions from a first diameter of approximately 0.375 inches (9.525 mm) to a second diameter of approximately 0.25 inches (6.35 mm). Further first tubing adaptor 112 has a length in a range from approximately 1.0 inches (25.4 mm) to 3.0 inches (76.2 mm) (e.g., a length of 2.0 inches (50.8 mm)). Alternatively, first tubing adaptor 112 may have any dimensions that enable flow loop 102 to function as described herein.

First tubing adaptor 112 is coupled in flow communication with a second tubing section 114. In this embodiment, second tubing section 114 is a section of flexible polymer tubing, such as TYGON® tubing. Further, in this embodiment, second tubing section 114 has a diameter of approximately 0.25 inches (6.35 mm) and a length in a range from approximately 6.0 inches (152.4 mm) to 120.0 inches (3048 mm) (e.g., a length of 180.0 inches (457.2 mm)), depending on the pressure conditions for the system. Alternatively, second tubing section 114 may have any composition and dimensions that enable flow loop 102 to function as described herein.

Second tubing section 114 is coupled in flow communication with a second tubing adaptor 116. In this embodiment, second tubing adaptor 116 transitions from a first diameter of approximately 0.25 inches (6.35 mm) to a second diameter of approximately 0.375 inches (9.525 mm). Further, second tubing adaptor 116 has a length in a range from approximately 1.0 inches (25.4 mm) to 3.0 inches (76.2 mm) (e.g., a length of 2.0 inches (50.8 mm)). Accordingly, second tubing adaptor 116 may be identical to first tubing adaptor 112, but installed in a reverse orientation. Alternatively, second tubing adaptor 116 may have any dimensions that enable flow loop 102 to function as described herein.

Second tubing adaptor 116 is coupled in flow communication with a third tubing section 118. In this embodiment, third tubing section 118 is a section of flexible polymer tubing, such as TYGON® tubing. Further, in this embodiment, third tubing section 118 has a diameter of approximately 3/8 inches (9.525 (mm)) and a length in a range from approximately 1.0 inches (25.4 mm) to 4.0 inches (101.6 mm) (e.g., a length of 2.0 inches (50.8 mm)). Accordingly, third tubing section 118 may be identical to first tubing section 110. Alternatively, third tubing section 118 may have any composition and dimensions that enable flow loop 102 to function as described herein.

In this embodiment, third tubing section 118 is coupled in flow communication with a flow probe 120. Flow probe 120 is operable to measure a flow rate through flow loop 102. By monitoring the flow rate, flow loop 102 can be modified to achieve a desired flow rate (e.g., 5 liters per minute (L/min)). For example, if the flow rate is too low, a pump speed (e.g., expressed in revolutions per minute (RPM)) of LVAD 104 may be increased. In contrast, if the flow rate is too high, the pump seed may be decreased. To facilitate measuring the flow rate, flow probe 120 may be coupled to a flow meter 121, such as a TRANSONIC® flow meter. TRANSONIC® is a registered trademark of Transonic Systems Inc., of Ithaca, N.Y.

Flow probe 120 is coupled in flow communication with a flow diverter 122. Flow diverter 122 channels blood from flow probe 120 into a blood reservoir 124 in flow communication with flow diverter 122. In this embodiment, flow diverter 122 is flexible polymer tubing, such as TYGON® tubing. Further, flow diverter 122 has a diameter of 0.375 inches (9.525 mm) and a length of approximately 6.0 inches (152.4 mm). At a distal end of flow diverter 122, side walls are removed to decrease blood flow and disperse blood flow more gently into blood reservoir 124. Alternatively, flow diverter 122 may have any composition and dimensions that enable flow loop 102 to function as described herein.

In this embodiment, flow diverter 122 includes an outlet 126 that is positioned below a surface 127 of a volume 128 of blood in blood reservoir 124. Accordingly, flow diverter 122 channels blood into blood reservoir 124 at a location below surface 127, which reduces or eliminates air bubbles and splashing of blood in blood reservoir 124. This facilitates maintaining the quality of blood flowing through flow loop 102 over repeated cycles. In this embodiment, outlet 126 is positioned from approximately 0.5 inches (12.7 mm) to 1.0 inches (25.4 mm) below surface 127. Alternatively, outlet 126 may have any suitable position that enables flow loop 102 to function as described herein.

A fourth tubing section 130 is connected in flow communication between blood reservoir 124 and LVAD 104 in this embodiment. Accordingly, blood flows from blood reservoir 124 into LVAD 104 through fourth tubing section 130. Once blood reaches LVAD 104, that blood is pumped into barbed outflow conduit 108, such that blood is continuously re-circulated through flow loop 102 while LVAD 104 is activated.

Accordingly, in this embodiment, blood is pumped, in sequence, from LVAD 104, through barbed outflow conduit 108, through first tubing section 110, through first tubing adaptor 112, through second tubing section 114, through second tubing adaptor 116, through third tubing section 118, through flow probe 120, through flow diverter 122, into blood reservoir 124, and back into LVAD 104.

In this embodiment, fourth tubing section 130 is a section of flexible polymer tubing, such as TYGON® tubing. Further, in this embodiment, fourth tubing section 130 has a diameter of approximately 0.75 inches (19.05 mm) and a length of approximately 2.0 inches (50.8 mm). Alternatively, fourth tubing section 130 may have any composition and dimensions that enable flow loop 102 to function as described herein.

Referring back to FIG. 1, blood behavior evaluation system 100 further includes a plurality of heat exchangers 140. Heat exchangers 140 assist in maintaining a temperature of blood in blood reservoirs 124, and accordingly, in flow loops 102. In this embodiment, blood behavior evaluation system 100 includes six heat exchangers 140. Alternatively, blood behavior evaluation system 100 may include any suitable number of heat exchangers 140.

As shown in FIG. 2, each blood reservoir 124 is positioned between and in contact with two heat exchangers 140. Each heat exchanger 140 is made of a thermally conductive material. For example, heat exchangers 140 may be aluminum. Further, to maintain a temperature of blood in blood reservoirs 124, a temperature-controlled fluid (e.g., water) is circulated through heat exchangers 140. In this embodiment, to maintain the temperature of blood to be consistent with the temperature of blood in a patient, the temperature-controlled fluid has a temperature of approximately 98.6° F. (37° C.). Alternatively, the temperature-controlled fluid may have any suitable temperature.

Blood behavior evaluation system 100 and flow loops 102, as described herein, provide several advantages over existing blood behavior evaluation systems, while still complying with ASTM standards.

For example, because of the configuration of flow loops 10, as compared to at least some known testing apparatus, flow loops 10 may require at least 50% less human blood to test an implantable medical device. Because flow loops 10 require less blood, a similar number of recirculations can be performed within a shorter amount of time, reducing test time as compared to at least some known testing apparatus. Reducing the test time also facilitates the usage of human blood for testing, with functional platelets, prior to a time-point at which they lose their function and/or disintegrate. Completing testing prior to that time-point provides more valid testing of the implantable medical device.

Decreasing the amount of blood (using the systems and methods described herein) also decreases the amount of non-device surfaces (e.g., plastic fittings, etc.) that the blood encounters, improving the integrity of the human blood.

At least some known testing apparatus use clamps downstream from the implantable medical device to achieve a pressure drop. However, the clamps introduce shear stresses, which may lead to blood degradation or artificial blood activation. In contrast, instead of using clamps, the systems and methods described herein achieve the pressure drop using tubing sections with different diameters (e.g., the first, second, and third tubing sections described herein). Smooth transitions between the tubing sections reduce or eliminate shear stresses, improving blood integrity. Further, the flow diverter in the blood loops described herein enables a smooth transition for blood entering the blood reservoir, further improving blood integrity.

To vary the pressure drop, the length and/or diameter of the tubing sections may be easily modified as needed. Further, the flow sensor described herein may be used to monitor and adjust the flow rate through the flow loops as needed Further, at least some known testing apparatus use a relatively bulky water bath to maintain blood temperature. In contrast, the systems and methods described herein use heat exchangers with temperature-controlled fluid to maintain blood temperature more easily and more accurately.

The blood behavior evaluation system described herein includes a plurality of flow loops, enabling different implantable medical devices to be tested head-to-head. Further, with the configuration described herein, it is relatively easy to swap out different implantable medical devices for each flow loop. The systems and methods described herein can also be used to test VAD and VAS components other than heart pumps themselves (e.g., inflow cannulae, outflow grafts, etc.).

For example, in some embodiments, the blood behavior evaluation system may be used to evaluate an outflow graft. As will be appreciated by those of skill in the art, in a LVAD VAS, an outflow graft is generally a conduit that channels blood flow from an LVAD to a patient's aorta. The outflow graft may be made of a fabric material, for example. Further, the outflow graft may have a diameter in a range from approximately 0.236 inches (6.0 mm) to 0.630 inches (16.0 mm), and a length in a range from approximately 2.0 inches (50.8 mm) to 20.0 inches (508.0 mm) in an unstretched, or unpressurized state. Outflow grafts may also be sealed with a sealant, or alternatively, unsealed. Further, portions of the outflow graft may be covered with a bend relief covering (e.g., made of an appropriate polymer and/or fabric material) to prevent kinking of the outflow graft.

To test an outflow graft, the outflow graft may be coupled within flow loop 102 in the same position as second tubing section 114 (i.e., coupled between first tubing adaptor 112 and second tubing adaptor 116). Accordingly, a flow rate through the outflow graft may be measured using flow probe 120.

In another embodiment, the outflow graft may be coupled in flow loop 102 directly between barbed outflow conduit 108 and flow diverter 122. For example, ends of the outflow graft may be sealed with polytetrafluoroethylene (PTFE) tape and fastened to barbed outflow conduit 108 and flow diverter 122. In this embodiment, first tubing section 110, first tubing adaptor 112, second tubing adaptor 116, third tubing section 118, and flow probe 120 are omitted from flow loop 102. Accordingly, to measure the flow rate through the outflow graft, a clamp-on flow probe may be attached to the exterior of the outflow graft (e.g., between bend relief covering sections).

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A flow loop for evaluating blood behavior when flowing through an implantable medical device, the flow loop comprising:
   the implantable medical device;
   a blood reservoir configured to contain a volume of blood and to supply blood from the volume of blood to the implantable medical device;
   a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter; and
   a flow diverter coupled in flow communication between the plurality of tubing sections and the blood reservoir, the flow diverter comprising an outlet that is configured to be positioned below a surface of the volume of blood.

2. The flow loop of claim 1, wherein the plurality of tubing sections comprises a third tubing section having the first diameter, and wherein the second tubing section is coupled in flow communication between the first tubing section and the third tubing section.

3. The flow loop of claim 2, further comprising a first tubing adaptor coupled in flow communication between the first tubing section and the second tubing section, wherein the first tubing adaptor transitions from the first diameter to the second diameter.

4. The flow loop of claim 3, further comprising a second tubing adaptor coupled in flow communication between the second tubing section and the third tubing section, wherein the second tubing adaptor transitions from the second diameter to the first diameter.

5. The flow loop of claim 1, wherein the implantable medical device comprises a barbed outflow conduit that couples the implantable medical device in flow communication with the first tubing section.

6. The flow loop of claim 1, wherein the implantable medical device comprises a left ventricular assist device.

7. The flow loop of claim 1, further comprising a flow probe coupled in flow communication between the plurality of tubing sections and the flow diverter, wherein the flow probe is configured to measure a flow rate of blood through the flow loop.

8. The flow loop of claim 1, wherein the first diameter is 0.375 inches (9.525 mm), and wherein the second diameter is 0.25 inches (6.35 mm).

9. The flow loop of claim 1, wherein the flow diverter comprises flexible polymer tubing.

10. A blood behavior evaluation system comprising:
    a plurality of heat exchangers; and
    a plurality of flow loops, wherein each flow loop of the plurality of flow loops comprises:
      an implantable medical device;
      a blood reservoir configured to contain a volume of blood and to supply blood from the volume of blood to the implantable medical device;
      a plurality of tubing sections coupled in flow communication between the implantable medical device and the blood reservoir, the plurality of tubing sections including a least a first tubing section having a first diameter and a second tubing section having a second diameter, wherein the second diameter is smaller than the first diameter; and
      a flow diverter coupled in flow communication between the plurality of tubing sections and the blood reservoir, the flow diverter comprising an outlet that is configured to be positioned below a surface of the volume of blood.

11. The blood behavior evaluation system of claim 10, wherein the plurality of tubing sections comprises a third tubing section having the first diameter, and wherein the second tubing section is coupled in flow communication between the first tubing section and the third tubing section.

12. The blood behavior evaluation system of claim 11, further comprising a first tubing adaptor coupled in flow communication between the first tubing section and the second tubing section, wherein the first tubing adaptor transitions from the first diameter to the second diameter.

13. The blood behavior evaluation system of claim 12, further comprising a second tubing adaptor coupled in flow communication between the second tubing section and the third tubing section, wherein the second tubing adaptor transitions from the second diameter to the first diameter.

14. The blood behavior evaluation system of claim 10, wherein the implantable medical device comprises a barbed outflow conduit that couples the implantable medical device in flow communication with the first tubing section.

15. The blood behavior evaluation system of claim 10, wherein the implantable medical device comprises a left ventricular assist device.

16. The blood behavior evaluation system of claim 10, further comprising a flow probe coupled in flow communication between the plurality of tubing sections and the flow diverter, wherein the flow probe is configured to measure a flow rate of blood through the flow loop.

17. The blood behavior evaluation system of claim 10, wherein the first diameter is 0.375 inches (9.525 mm), and wherein the second diameter is 0.25 inches (6.35 mm).

18. The blood behavior evaluation system of claim 10, wherein the flow diverter comprises flexible polymer tubing.

19. The blood behavior evaluation system of claim 10, wherein the blood reservoir of each flow loop is positioned between and in contact with two heat exchangers of the plurality of heat exchangers.

20. The blood behavior evaluation system of claim 10, wherein each heat exchanger comprises a thermally conductive body configured to circulate a temperature-controlled fluid therethrough.

* * * * *